United States Patent [19]
Binderup et al.

[11] Patent Number: 4,870,063
[45] Date of Patent: Sep. 26, 1989

[54] BISPHOSPHONIC ACID DERIVATIVES, THEIR PRODUCTION AND USE

[75] Inventors: Ernst T. Binderup, Tåstrup; Sven Liisberg, Vedbæk, both of Denmark

[73] Assignee: Leo Pharmaceutical Products Ltd. A/S, Ballerup, Denmark

[21] Appl. No.: 90,980
[22] PCT Filed: Dec. 10, 1986
[86] PCT No.: PCT/DK86/00132
   § 371 Date: Aug. 10, 1987
   § 102(e) Date: Aug. 10, 1987
[87] PCT Pub. No.: WO87/03598
   PCT Pub. Date: Jun. 18, 1987

[30] Foreign Application Priority Data

Dec. 12, 1985 [GB] United Kingdom ............... 8530603

[51] Int. Cl.$^4$ .................. C07D 279/12; C07F 9/65; A61K 31/67; A61K 31/54
[52] U.S. Cl. ....................... 514/79; 544/57; 540/467; 540/544
[58] Field of Search ................ 544/57; 540/542, 467; 514/212, 222, 79

[56] References Cited

U.S. PATENT DOCUMENTS 4,264,768  4/1981  Quinlan ................... 544/57
4,311,663  1/1982  Quinlan ................... 544/57

FOREIGN PATENT DOCUMENTS 3232998  3/1984  Fed. Rep. of Germany ........ 544/57

Primary Examiner—John M. Ford
Attorney, Agent, or Firm—Cushman, Darby & Cushman

[57] ABSTRACT

Novel compounds of the formula I

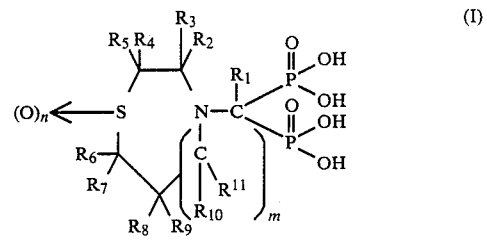

in which $R_1$–$R_{11}$ can be the same or different and stand for hydrogen, a straight or branced aliphatic or alicyclic $C_1$–$C_{10}$ hydrocarbon radical, an aryl or an aryl-$C_1$–$C_4$-alkyl radical; n is zero or one, and m is zero, one or two; or $R_2$ and $R_4$ when taken together form a saturated aliphatic 5-, 6- or 7-membered ring which may be substituted with one or more $C_1$–$C_4$ alkyl radicals; and pharmaceutically acceptable salts and easily hydroyzable esters thereof, methods for producing said new compounds, pharmaceutical compositions containing the new compounds, dosage units of the compositions, and methods of treating patients using said compositions and dosage units.

The present compounds are valuable in the human and veterinary practice by reducing bone resorption and surprisingly also stimulating bone alkaline phosphatase. A substantial increase in bone mass is actually observed during treatment with the present compounds.

8 Claims, No Drawings

BISPHOSPHONIC ACID DERIVATIVES, THEIR PRODUCTION AND USE

The present invention relates to hitherto unknown compounds useful in the human and veterinary therapy, to pharmaceutically acceptable salts and easily hydrolyzable esters thereof, to methods for producing said new compounds, to pharmaceutical compositions containing the new compounds, to dosage units of the compositions, and to methods of treating patients using said compositions and dosage units.

The present compounds have the formula I

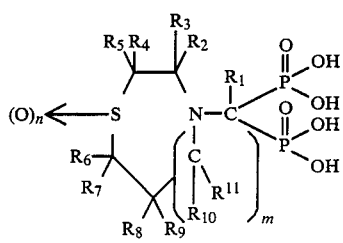

in which $R_1$–$R_{11}$ can be the same or different and stand for hydrogen, a straight or branched aliphatic or alicyclic $C_1$–$C_{10}$ hydrocarbon radical, an aryl or an aryl-$C_1$–$C_4$-alkyl radical; n is zero or one, and m is zero, one or two.

In addition $R_2$ and $R_4$ when taken together can form a saturated aliphatic 5-, 6- or 7-membered ring which may be substituted with one or more $C_1$–$C_4$-alkyl radicals.

In particular, $R_1$–$R_{11}$ stand for hydrogen, $C_1$–$C_5$-alkyl, or phenyl.

The invention comprises all possible stereoisomeric forms of compounds of formula I as well as mixtures thereof.

As stated above, the invention also relates to salts of the compounds of formula I which are acids and thus form salts with bases. As examples of salts formed with pharmaceutically acceptable, non-toxic bases, mention may be made of alkali metal salts and alkaline earth metal salts, such as lithium, sodium, potassium, magnesium, calcium salts, as well as salts with ammonia and suitable non-toxic amines, such as lower alkylamines, e.g. triethylamine, lower alkanolamines, e.g. diethanolamine or triethanolamine, procaine, cycloalkylamines, e.g. dicyclohexylamine, benzylamines, e.g. N-methylbenzylamine, N-ethylbenzylamine, N-benzyl-β-phenethylamine, N,N'-dibenzylethylenediamine or dibenzylamine, and heterocyclic amines, e.g. morpholine, N-ethylpiperidine and the like.

The esters of the present compounds are in vivo easily hydrolyzable. Examples of such ester forming residues are alkanoyloxymethyl of three to six carbon atoms, 1-(alkanoyloxy)ethyl of four to severn carbon atoms, 1-methyl-1-(alkanoyloxy)ethyl of five to eight carbon atoms, alkoxycarbonyloxymethyl of three to six carbon atoms, 1-(alkoxycarbonyloxy)ethyl of four to seven carbon atoms, 1-methyl-1-(alkoxycarbonyloxy)ethyl of five to eight carbon atoms, 3-phthalidyl, 4-crotonolactonyl, γ-butyrolacton-4-yl, (2-oxo-1,3-dioxolen-4-yl)methyl, (5-methyl-2-oxo-1,3-dioxolen-4-yl)methyl, and (5-phenyl-2-oxo-1,3-dioxolen-4-yl)methyl as well as dialkylaminoalkyl, acetonyl, and methoxymethyl.

The normal bones are living tissues undergoing constant resorption and redeposition of calcium, with the net effect of maintenance of a constant mineral balance. The dual process is commonly called "bone turnover". In normal growing bones, the mineral deposition exceeds the mineral resorption, whereas in certain pathological conditions, bone resorption exceeds bone deposition resulting in e.g. hypercalcemia, for instance due to malignancy or primary hyperparathyroidism, or in osteoporosis. In other pathological conditions the calcium deposition may take place in undesirable amounts and areas leading to e.g. osteoarthritis, rheumatoid arthritis, kidney or bladder stones, atherosclerosis, and Paget's disease which is a combination of an abnormal high bone resorption followed by an abnormal calcium deposition.

Most of the currently available therapeutic agents for the treatment of osteoporosis, e.g. estrogens and calcitonin, act by reducing bone resorption in the osteoporotic patient. Since bone fracture is a severe problem in osteoporosis, the ideal therapeutic agent should be able to increase bone mass to a level which exceeds the fracture threshold.

Experiments in rats have shown that the compounds of the present invention like known bisphosphonates (e.g. 1-hydroxyethylidene-1,1-bisphosphonic acid (etidronate) and 3-amino-1-hydroxypropylidene-1,1-bisphosphonic acid (APD)) reduce bone resorption as shown by their inhibition of the urinary excretion of hydroxyproline, but in contrast to these known compounds which also inhibit bone alkaline phosphatase, the new compounds of this invention surprisingly stimulate bone alkaline phosphatase, indicating a stimulation of the bone forming cells—the osteoblasts—and a substantial increase in bone mass is actually observed during treatment with the present compounds.

The compounds of the present invention (n=0) may be prepared from a compound of formula II

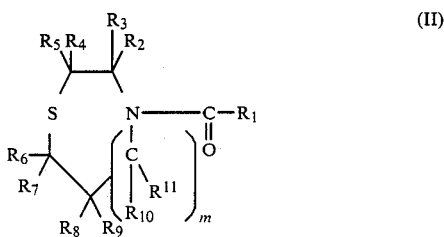

where $R_1$–$R_{11}$ and m have the meanings mentioned above. The compounds of formula II are either known or may be prepared in analogy with the known compounds. They are transformed into acid amide chlorides of formula III by treatment with e.g. phosgene or oxalyl chloride

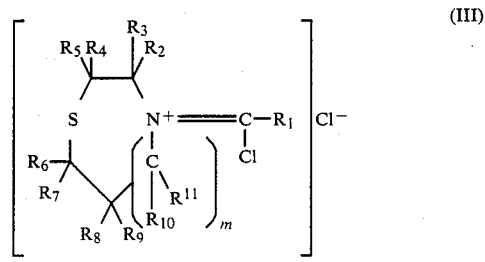

($R_1$–$R_{11}$ and m as defined above).

Reaction of compounds of formula III with trialkylphosphites leads to tetraalkyl esters of formula IV

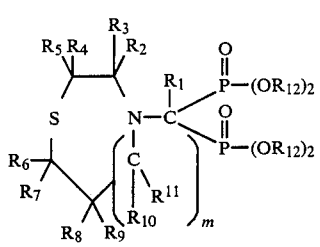

where $R_1$–$R_{11}$ and m have the meanings defined above and $R_{12}$ is a $C_1$–$C_4$-alkyl radical, preferably methyl or ethyl, or a benzyl or a substituted benzyl radical.

Cleavage of the esters of formula IV by hydrolysis, e.g. with boiling hydrochloric acid, or by hydrogenolysis, leads to the compounds of formula I (n=0).

The esters may also be cleaved by an alternative method described in Jour. f. prakt. Chemie 320, 344 (1978). Treatment with bromotrimethylsilane at room temperature or moderately elevated temperature leads to a tetra-trimethylsilyl ester which is easily cleaved with water or alcohol to yield the free acid or formula I.

Alternatively, compounds of formula I (n=0) may be prepared by reacting compounds of formula II with phosphorous acid and phosphorus trichloride followed by hydrolysis of the reaction mixture.

Compounds of formula I in which n=1 may be prepared by oxidation of compounds of formula I or IV (n=0) with the well known reagents for the preparation of sulfoxides from sulfides, e.g. 3-chloroperbenzoic acid or hydrogen peroxide, optionally followed by ester cleavage.

Easily hydrolyzable esters of the compounds of formula I may be prepared by reacting a salt, e.g. a silver salt or a quaternary ammonium salt, of a compound of formula I with a reactive halide corresponding to the desired ester.

Tetra-esters may be cleaved by reaction with an iodide, e.g. sodium iodide, to form di-esters of the compounds of formula I.

The present compounds are as mentioned above intended for use in pharmaceutical compositions which are useful in the treatment of osteoporosis, rheumatoid arthritis and other arthritic disorders, atherosclerosis, hypercalcemia due to malignancies or primary hyperparathyroidism, Paget's disease, and other conditions with an abnormal calcium balance.

The present compounds may also be used in toothpastes in order to prevent calcium deposition in the form of dental calculus or in order to protect against calcium resorption due to acid dissolution.

The amount required of a compound of formula I (hereinafter referred to as the active ingredient) for therapeutic effect will, of course, vary both with the particular compound, the route of administration and the mammal under treatment. A suitable dose of a compound of formula I for a mammal suffering from e.g. a hypercalcemic condition as defined hereinbefore is 0.001 to 25 mg per kilogram bodyweight, the most preferred dosage being 0.002 to 10 mg/kg of mammal bodyweight, for example 0.005 to 5 mg/kg; administered once or more times daily.

In the case of the profylactic treatment of e.g. postmemopausal osteoporosis, a suitable dose of a compound of formula (I) is 0.001 to 10 mg per kilogram bodyweight, the most preferred dosage being 0.002 to 5 mg/kg of mammal bodyweight.

While it is possible for an active ingredient to be administered alone as the pure compound, it is preferable to present it as a pharmaceutical formulation. Conveniently, the active ingredient comprises from 0.1% to 99.9% by weight of the formulation. Conveniently, dosage units of a formulation contain between 0.1 mg and 1 g of the active ingredient. For topical administration, the active ingredient preferably comprises from 1% to 2% by weight of the formulation but the active ingredient may comprise as much as 10% w/w.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier and optionally other therapeutic ingredient(s). The carrier(s) must be "acceptable" in the sense of being compatible with the other ingredients of the formulations and not deleterious to the recipient thereof.

The formulations include those in a form suitable for oral, rectal, parenteral (including subcutaneous, intramuscular and intravenous), or topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administrations may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations suitable for topical administration include liquid or semi-liquid preparations such as liniments, lotions, applications; oil-in-water or water-in-oil emulsions such as creams, ointments or pastes, including tooth-pastes; or solutions or suspensions such as drops.

In addition to the aforementioned ingredients, the formulations of this invention may include one or more additional ingredients such as diluents, buffers, flavouring agents, binders, surface active agents, thickeners, lubricants, preservatives, e.g. methylhydroxybenzoate (including anti-oxidants), emulsifying agents and the like.

The compositions may further contain other therapeutically active compounds usually applied in the treatment of the above mentioned pathological conditions, for instance vitamin $D_2$ and $D_3$ and hydroxylated derivatives, e.g. 1α-hydroxy-vitamin $D_3$, 1α-hydroxy-vitamin $D_2$, 1α,25-dihydroxy-vitamin $D_3$, 1α,25-dihydroxy-vitamin $D_2$, calcitonin (human, porcine or salmon), mitramycin, sodium fluoride, estrogens, and non-steroid antiinflammatory drugs, e.g. acetylsalicyclic acid, indomethacin, naprosyn, and timegadine.

According to the invention, the present compounds are administered to a patient suffering from one of the above mentioned pathological conditions in a daily dose (for adults) from 0.07 mg to 1750 mg, preferably from 0.15–1000 mg, and in the veterinary practice correspondingly in daily doses from 0.001 to 25 mg/kg bodyweight.

The invention will now be further described in the following non-limiting Preparations and Examples:

PREPARATION 1

5,5-Dimethyl-3-thiomorpholinone 2,2-Dimethylaziridine (35.5 g) was added dropwise with stirring at 100° C. to methyl mercaptoacetate (53 g) during 1.5 hours. After a further 2 hours at 100° C., the mixture was cooled and crystallized from ethyl acetate. Melting point: 151–152° C.

PREPARATION 2

3,3-Dimethyl-thiomorpholine 5,5-Dimethyl-3-thiomorpholinone (50 g) was added in portions to a stirred suspension of lithium aluminium hydride (25 g) in tetrahydrofuran (1000 ml). After 20 hours reflux, unreacted lithium aluminium hydride was destroyed by the addition of sodium sulfate decahydrate. The mixture was filtered, and the filtrate was evaporated in vacuo. Distillation in vacuo gave the title compound with boiling point 71°–72° C./15 mmHg.

PREPARATION 3

2,5,5-Trimethyl-3-thiomorpholinone

This compound was obtained from 2,2-dimethylaziridine and methyl-2-mercaptopropionate as described in Preparation 1.

Melting point: 137°–138° C.

PREPARATION 4

2,5,5-Trimethyl-thiomorpholine

This compound was prepared as described in Preparation 2 by substituting 2,5,5-trimethyl-3-thiomorpholinone for 5,5-dimethyl-3-thiomorpholinone. Boiling point: 76°–77° C./15 mmHg.

PREPARATION 5

2-(1-Butyl)-3-thiomorpholinone

Potassium hydroxide (56 g) was added to a suspension of cysteamine, hydrochloride (56.6 g) in absolute ethanol (300 ml) followed by dropwise addition of ethyl 2-bromohexanoate (111.5 g). When the exothermic reaction ceased, the mixture was refluxed for 3 hours and filtered. Concentration of the filtrate in vacuo gave the title compound as a viscous oil which was used in the next step without purification.

PREPARATION 6

2-(1-Butyl)-thiomorpholine, hydrochloride

This compound was prepared as described in Preparation 2 by substituting 2-(1-butyl)-3-thiomorpholinone for 5,5-dimethyl-3-thiomorpholinone.

A solution of the crude 2-(1-butyl)-thiomorpholine in ether was treated with an excess of hydrogen chloride in ether to yield a crystalline hydrochloride with melting point 104° C.

Microanalysis: Calculated: C: 49.08, H: 9.27, N: 7.16, S: 16.38, Cl: 18.11. Found: C: 49.12, H: 9.34, N: 7.09, S: 16.19, Cl: 18.00.

PREPARATION 7

N-Formyl-thiomorpholine

Chloral (10 ml) was added dropwise to a solution of thiomorpholine (10 g) in tetrachloromethane (50 ml), and the resulting mixture was refluxed for 1 hour. Distillation in vacuo gave N-formyl-thiomorpholine with boiling point 140° C./15 mmHg. When kept at room temperature, the pure product formed low melting crystals.

PREPARATION 8

By following the procedure described in Preparation 7 and substituting the appropriately substituted thiomorpholine for thiomorpholine itself, the following compounds were prepared:

N-Formyl-2-methyl-thiomorpholine: B.p.: 141°–142° C./15 mmHg

N-Formyl-3-methyl-thiomorpholine: B.p.: 146°–147° C./15 mmHg

N-Formyl-3,3-dimethyl-thiomorpholine: B.p.: 155°–156° C./15 mmHg

N-Formyl-2,5,5-trimethyl-thiomorpholine: B.p.: 154°–155° C./15 mmHg

N-Formyl-2-ethyl-thiomorpholine: B.p. 75° C./1.5 mmHg

N-Formyl-2,2-dimethyl-thiomorpholine: B.p.: 75°–76° C./1 mmHg

N-Formyl-3-ethyl-thiomorpholine: B.p.: 145°–146° C./15 mmHg

N-Formyl-2-(1-butyl)-thiomorpholine: B.p.: 160°–162° C./15 mmHg

N-Formyl-2-phenyl-thiomorpholine: B.p.: 148°–150° C./1 mmHg

PREPARATION 9

N-Formyl-2,6-dimethyl-thiomorpholine

Piperidine (10 ml) and 10 ml of a 40% solution of benzyltrimethylammoniumhydroxide in methanol were added to a solution of N-formyl-diallylamine (55 g) in methanol (200 ml). Hydrogen sulfide (50 g) was introduced into the resulting solution, and unreacted hydrogen sulfide was kept at reflux for 7 hours by means of "cold finger". The mixture was left at room temperature for 48 hours, flushed with nitrogen, diluted with ether, and washed with water. The organic phase was dried, and the solvent evaporated in vacuo. Distillation of the residue gave the title compound with boiling point 145° C./15 mmHg.

PREPARATION 10

N-Formyl-3-ethyl-2-methyl-thiomorpholine

Cysteamine, hydrochloride (68.2 g, 0.6 mole) was added to an ice-cold stirred solution of sodium (27.6 g, 1.2 mole) in ethanol (1000 ml). α-Bromo-diethyl ketone (99 g, 0.6 mole) was then added slowly in a nitrogen atmosphere while the temperature was kept below 25° C.

After stirring for 2 hours, the mixture was filtered, and the filtrate evaporated in vacuo to leave an oil which was taken up in water (300 ml) and extracted with ether (2×500 ml). The organic phase was separated, dried and evaporated to give an oil which was distilled in vacuo. The distillate (b.p. 70° C./1 mmHg) wsa heated to 140° C. with stirring, and formic acid (100 ml) was added at such a rate that the temperature was kept at 135°–140° C. without external heating. After standing overnight at room temperature, the stirred mixture was slowly treated with 40% potassium hydroxide (200 ml) and extracted with ether (2×500 ml). The organic phase was dried and concentrated to about 500 ml. Chloral (80 ml) was added, and the mixture was refluxed for 1 hour, cooled and evaporated to leave an oil which was distilled in vacuo to give the title compound with b.p.: 102°–104° C./1 mmHg.

PREPARATION 11

By following the procedure described in Preparation 10 and substituting the appropriate α-bromo ketones for α-bromo-diethyl ketone, the following compounds were prepared:
N-Formyl-2,3-dimethyl-thiomorpholine: B.p.: 88°–90° C./1 mmHg
N-Formyl-2-isopropyl-3-methyl-thiomorpholine: B.p. 125°–126° C./1 mmHg
N-Formyl-2-isobutyl-3-methyl-thiomorpholine: B.p. 115°–116° C./1 mmHg
N-Formyl-perhydro-1,4-benzothiazine: M.p.: 70°–71° C. B.p.: 128°–130° C./1 mmHg.
N-Formyl-7-methyl-perhydro-1,4-benzothiazine: M.p.: 135°–136° C.
N-Formyl-3-isobutyl-thiomorpholine: B.p.: 110°–114° C./1 mmHg

PREPARATION 12

By using the appropriate starting materials and following the procedures described in Preparations 1, 2 and 7, the following compounds were prepared.
N-Formyl-2-isobutyl-thiomorpholine: B.p.: 150°–155° C./15 mmHg
N-Formyl-2,5-dimethyl-thiomorpholine: B.p.: 142°–143° C./15 mmHg

PREPARATION 13

By repeating the procedure of Preparation 10 and replacing α-bromo-diethyl ketone by the appropriate α-bromo ketones, the following compounds were prepared.
N-Formyl-3-(n-propyl)-thiomorpholine
N-Formyl-3-isopropyl-thiomorpholine B.p.: 95°–96° C./1 mmHg
N-Formyl-3-phenyl-thiomorpholine
N-Formyl-2-ethyl-3-methyl-thiomorpholine
N-Formyl-3-(n-butyl)-thiomorpholine
N-Formyl-2-ethyl-3-propyl-thiomorpholine B.p.: 122°–123° C./1 mmHg
N-Formyl-2-isopropyl-3-isobutyl-thiomorpholine B.p.: 122°–123° C./1 mmHg
N-Formyl-2,2-dimethyl-3-isopropyl-thiomorpholine B.p.: 116°–117° C./1 mmHg
N-Formyl-3-cyclopropyl-thiomorpholine B.p.: 109°–110° C./1 mmHg
N-Formyl-3-nonyl-thiomorpholine B.p.: 147°–148° C./1 mmHg
N-Formyl-3-tert-butyl-thiomorpholine B.p.: 113°–114° C./1 mmHg
N-Formyl-2,2-dimethyl-3-phenyl-thiomorpholine
N-Formyl-3-methyl-2-phenyl-thiomorpholine
N-Formyl-3-isopentyl-thiomorpholine
N-Formyl-3-cyclohexyl-thiomorpholine
N-Formyl-2-phenyl-3-benzyl-thiomorpholine
N-Formyl-2-pentyl-3-hexyl-thiomorpholine

PREPARATION 14

3-tert-Butyl-thiomorpholine

This compound was prepared as described in Preparation 10 by using bromomethyl tert-butyl ketone instead of α-bromo-diethyl ketone and by omitting the treatment with chloral. The title compound was distilled in vacuo, b.p.: 73°–74° C./1 mmHg.

PREPARATION 15

(+)-3-tert-Butyl-thiomorpholine 3-tert-Butyl-thiomorpholine (159 g, racemic form described in Preparation 14) was added to a hot solution of (+)-tartaric acid (150 g) in water (100 ml). The mixture was left overnight and filtered. The crystalline salt which showed $[\alpha]_D^{20} = +20°$ (c=1, H$_2$O) was recrystallized repeatedly from water until $[\alpha]_D^{20} = +32°$ (c=1, H$_2$O). The free base was liberated with an excess of 30% potassium hydroxide and taken up in ether. The solution was dried and evaporated to leave the title compound as an oil with $[\alpha]_D^{20} = +36.1°$ (c=1, EtOH).

PREPARATION 16

(−)-3-tert-Butyl-thiomorpholine 3-tert-Butyl-thiomorpholine—liberated from the combined filtrates obtained in Preparation 15 during the preparation of the tartrate—was treated with (−) tartaric acid in water. The resulting tartrate was recrystallized until $[\alpha]_D^{20} = -31.4°$ (c=1, H$_2$O). The free base showed $[\alpha]_D^{20} = -36.0°$ (c=1, EtOH).

PREPARATION 17

The compounds prepared in Preparation 15 and 16 were formylated with chloral as described in Preparation 7 to yield
(+)-N-formyl-3-tert-butylthiomorpholine $[\alpha]_D^{20} = +108°$ (c=1, EtOH) and
(−)-N-formyl-3-tert-butylthiomorpholine $[\alpha]_D^{20} = -107°$ (c=1, EtOH).

PREPARATION 18

By following the procedures described in Examples 15, 16 and 17 other substituted thiomorpholines may be resolved into the enantiomers and subsequently formylated to form e.g.
(+)-N-formyl-3-isobutylthiomorpholine
(−)-N-formyl-3-isobutylthiomorpholine

PREPARATION 19

N-Formyl-tetrahydro-1,4-thiazepin-3-one

To a solution of sodium (23 g) in absolute ethanol (1 l) was added ethyl thioglycolate (60.1 g) and 3-bromopropylamine, hydrobromide (109.5 g). After reflux for 12 hours, the mixture was cooled and filtered. The filtrate was evaporated in vacuo, and the residue was crystallized from ethanol to yield tetrahydro-1,4-thiazepin-3-one with m.p. 145°–148° C. 60 g of this product was added in portions to a stirred suspension of lithium aluminium hydride (25 g) in tetrahydrofuran (2.5 l). The mixture was kept at 45°–50° C. for 2 hours followed by reflux for a further 2 hours. After cooling a mixture of water (62 ml) and tetrahydrofuran (250 ml) was added dropwise with stirring. Filtration and evaporation of the filtrate gave a residue which was dissolved in ether (250 ml), dried over magnesium sulfate, filtered and treated dropwise with chloral (40 ml). After reflux for 1 hour the solvent was evaporated, and the residue distilled in vacuo to yield the title compound with b.p. 158°–159° C./18 mmHg.

PREPARATION 20

N-Formyl-2-methyl-tetrahydro-1,4-thiazepin-3-one

This compound was prepared by following the procedure of Preparation 19, but substituting ethyl 2-mercaptopropionate for ethyl thioglycolate. 2-Methyl-tetrahydro-1,4-thiazepin-3-one with m.p. 192°–193° C. was isolated as an intermediate. The title compound was colourless oil with b.p. 104°–105° C./1 mmHg.

EXAMPLE 1

(4-Thiomorpholinylmethylene)-bisphosphonic acid

Oxalyl chloride (16.6 ml) was added dropwise at 0° C. to a stirred solution of N-formyl-thiomorpholine (26.2 g) in methylene chloride (200 ml). The mixture was stirred at room temperature until the gas evolution ceased (about 5 hours later). Triethyl phosphite (66 ml) was then added during 1.5 hours at room temperature. Unreacted triethyl phosphite was removed in vacuo, and the residue was refluxed with 20% hydrochloric acid (150 ml) for 3 hours. The mixture was evaporated to dryness in vacuo, and the residue was stirred with acetone. The crystalline product was filtered and recrystallized from water. M.p.: >250° C. (dec.).

Microanalysis: Calculate: C: 21.67, H: 4.73, N: 5.05, S: 11.57. Found: C: 21.56, H: 4.77, N: 4.95, S: 11.35.

NMR (NaOD, TMS=0.0 ppm as reference): $\delta$=2.8–3.1 (m, 4H); 3.21 (t, J=18 Hz, 1H) and 3.7–4.0 (m, 4H) ppm.

EXAMPLE 2

By following the procedure described in Example 1 and substituting the appropriate N-formyl-derivatives described in Preparations 8, 9, 10, 11 and 12 for N-formyl-thiomorpholine, the following compounds were prepared:

(2-Methyl-4-thiomorpholinylmethylene)-bisphosphonic acid: M.p.: >250° C. (dec). NMR (NaOD, HDO=4.66 ppm as reference): $\delta$=1.20 (d, J=6.8 Hz, 3H) and 2.7–3.8 (m, 8H) ppm.

(2-(1-Butyl)-4-thiomorpholinylmethylene)-bisphosphonic acid: M.p.: 226°–227° C. NMR (NaOD, HDO=4.66 ppm as reference): $\delta$=0.78 (t, 3H); 1.28 (bs, 6H) and 2.4–3.6 (m, 8H) ppm.

(2-Ethyl-4-thiomorpholinylmethylene)-bisphosphonic acid: M.p.: 237°–238° C. NMR (NaOD, HDO=4.66 ppm as reference): $\delta$=0.85 (m, 3H); 1.40 (m, 2H) and 2.4–3.4 (m, 8H) ppm.

(3,3-Dimethyl-4-thiomorpholinylmethylene)-bisphosphonic acid: NMR (NaOD, HDO=4.66 ppm as reference): $\delta$=1.52 (bs, 6H); 2.91 (bs, 2H) and 2.8–4.0 (m, 5H) ppm.

(2,5,5-Trimethyl-4-thiomorpholinylmethylene)-bisphosphonic acid: M.p.: 200° C. (dec.). NMR (NaOD, HDO=4.66 ppm as reference): $\delta$=1.20 (d, J=7 Hz, 3H); 1.48 (s, 3H); 1.58 (s, 3H) and 2.6–4.0 (m, 6H) ppm.

(2-Phenyl-4-thiomorpholinylmethylene)-bisphosphonic acid: M.p.: 250° C. (dec.). NMR (NaOD, HDO=4.66 ppm as reference): $\delta$=2.4–3.6 (m, 7H); 4.0 (m, 1H) and 7.25 (m, 5H) ppm.

(2,2-Dimethyl-4-thiomorpholinylmethylene)bisphosphonic acid: M.p.: 246°–247° C. NMR (NaOD, HDO=4.66 ppm as reference): $\delta$=1.37 (s, 6H); 3.00 (bt, 2H); 3.41 (t, J=18.5 Hz, 1H); 3.61 (bs, 2H) and 3.75 (bt, 2H) ppm.

(3-Methyl-4-thiomorpholinylmethylene)-bisphosphonic acid: M.p.: 221°–222° C. NMR (NaOD, HDO=4.66 ppm as reference): $\delta$=1.46 (d, J=6.5 Hz, 3H); 2.4–3.2 (m, 4H) and 3.5–4.3 (m, 4H) ppm.

(3-Ethyl-4-thiomorpholinylmethylene)-bisphosphonic acid: M.p.: 226°–227° C. NMR (NaOD, TMS=0.0 ppm as reference): $\delta$=1.01 (t, 3H); 2.00 (m, 2H); 2.9–3.2 (m, 4H); 3.5 (t, 1H) and 3.7–4.3 (m, 3H) ppm.

(2,6-Dimethyl-4-thiomorpholinylmethylene)-bisphosphonic acid: M.p.: 245° C. (dec.). NMR (NaOD, TMS=0.0 ppm as reference): $\delta$=1.4 (m, 6H) and 3.1–4.0 (m, 7H) ppm.

(2,5-Dimethyl-4-thiomorpholinylmethylene)-bisphosphonic acid, monohydrate: M.p.: 219°–220° C. NMR (NaOD, TMS=0.0 ppm as reference): $\delta$=1.4–1.8 (m, 6H), 3.2 (d, 2H) and 3–4.5 (m, 5H) ppm, (2,3-Dimethyl-4-thiomorpholinylmethylene)-bisphosphonic acid: M.p.: 200°–202° C. NMR (D$_2$O, HDO=4.66 ppm as reference): $\delta$=1.18 (m, 3H), 1.43 (m, 3H) and 2.5–4.3 (m, 7H) ppm.

(2-Isobutyl-4-thiomorpholinylmethylene)-bisphosphonic acid: M.p.: 238° C. (dec.). NMR (NaOD, HDO=4.66 ppm as reference): $\delta$=0.83 (d, 6H); 1.35 (t, 2H); 1.7 (m, 1H) and 2.75–4.0 (m, 8H) ppm.

(2-Isobutyl-3-methyl-4-thiomorpholinylmethylene)-bisphosphonic acid, disodium salt: NMR (D$_2$O, TMS=0.0 ppm as reference): $\delta$=0.93 (m, 6H); 1.1–2 (m, 6H) and 2.9–4.3 (m, 7H) ppm.

(3-Ethyl-2-methyl-4-thiomorpholinylmethylene)-bisphosphonic acid: NMR (NaOD, HDO=4.66 ppm as reference): $\delta$=0.83 (t, 3H); 1.17 (m, 3H); 1.8–2.1 (m, 2H) and 2.5–4.25 (m, 7H) ppm.

(2-Isopropyl-3-methyl-4-thiomorpholinylmethylene)-bisphosphonic acid: M.p.: 214°–216° C. NMR (NaOD, HDO=4.66 ppm as reference): $\delta$=0.95 (m, 6H); 1.47 (d, 3H); 1.55 (m, 1H); 3.46 (t, J=16 Hz, 1H) and 2.6–4.7 (m, 6H) ppm.

[(7-Methyl-perhydro-1,4-benzothiazin-4-yl)-methylene]-bisphosphonic acid: M.p.: 256°–257° C. NMR (NaOD, HDO=4.66 ppm as reference): $\delta$=0.80 (d, 3H), 0.9–2.0 (m, 6H), 2.2–2.5 (m, 1H) and 2.6–4.3 (m, 7H) ppm.

[(Perhydro-1,4-benzothiazin-4-yl)-methylene]-bisphosphonic acid: M.p.: 257°–258° C. NMR (NaOD, HDO=4.66 ppm as reference): $\delta$=0.9–2.0 (m, 7H); 2.2–3.8 (m, 7H) and 4.15 (bd, 1H) ppm.

(3-Isobutyl-4-thiomorpholinylmethylene)-bisphosphonic acid: M.p.: 237°–238° C. (dec.). NMR (NaOD, TMS=0.0 ppm as reference): δ0.97 (bm, 6H); 1.4–2.0 (m, 3H); 2.5–3.2 (m, 4H) and 3.3–4.0 (m, 4H) ppm.

EXAMPLE 3

[1-(4-Thiomorpholinyl)-ethylidene]-bisphosphonic acid, bis-benzylamine salt

A mixture of N-acetyl-thiomorpholine (14.5 g) and phosphorous acid (24.6 g) was heated at 100° C. for 3 hours. Phosphorus trichloride (41.1 g) was added dropwise with stirring and after reflux for 3 hours, water (80 ml) was added slowly, and the mixture was kept at 100° C. for 3 hours. Filtration and evaporation of the filtrate gave an oil which was taken up in ethanol. The title compound was precipitated by the addition of ether. The crude product was transformed into a bis-benzylamine salt with m.p.: 223°–224° C. NMR (D$_2$O, HDO=4.66 ppm as reference): δ=1.51 (t, J=13 Hz, 3H); 2.95 (t, 4H); 3.85 (m, 4H); 4.07 (s, 4H) and 7.36 (s, 10H) ppm.

EXAMPLE 4

Tetrabenzyl (4-thiomorpholinylmethylene)-bisphosphonate sulfoxide

Oxalyl chloride (0.85 ml) was added dropwise at −10° C. to a stirred solution of N-formyl-thiomorpholine (1.31 g) in tetrahydrofuran (10 ml), and the mixture was stirred at −10° C. for 1 hour.

A solution of sodium dibenzylphosphite in tetrahydrofuran (20 ml) (prepared from dibenzylphosphite (8.4 g) and 55% NaH (1.08 g)) was added, and after stirring for 1 hour the solvent was evaporated and the remaining oil distributed between water and methylene chloride. The organic phase was dried and evaporated to leave an oil which was purified by flash chromatography on silica gel (ether:acetone 90:10 as eluent) to yield tetrabenzyl (4-thiomorpholinylmethylene)-bisphosphonate (1.27 g) which was taken up in alcoholfree chloroform (15 ml). This solution was cooled in ice and treated dropwise with a solution of 90% 3-chloroperbenzoic acid (0.38 g) in alcoholfree chloroform (5 ml). The ice bath was removed, and after stirring for a further 90 minutes the solvent was removed in vacuo, and the residue was purified by chromatography on silica gel to give the title compound as a colourless oil. NMR (CDCl$_3$, TMS=0.0 ppm as reference): δ=2.62 (bt, 4H); 3.0 (bm, 2H); 3.36 (t, J=25 Hz, 1H); 3.60 (bm, 2H); 5.04 (m, 8H) and 7.30 (s, 20H) ppm.

EXAMPLE 5

(4-Thiomorpholinylmethylene)-bisphosphonic acid sulfoxide

To a solution of tetrabenzyl (4-thiomorpholinylmethylene)-bisphosphonate sulfoxide (1 g) in ethyl acetate (15 ml) were added water (15 ml) and 10% palladium on carbon (1 g). The resulting mixture was shaken vigorously in a hydrogen atmosphere until the consumption of hydrogen ceased. The catalyst was removed by filtration, and the aqueous phase was separated and freeze-dried to yield the title compound as an amorphous powder. NMR (NaOD, HDO=4.66 ppm as reference): δ=2.75 (t, J=22.6 Hz, 1H): 2.7–3.25 (m, 6H) and 3.3–3.7 (m, 2H) ppm.

EXAMPLE 6

The procedure of Example 1 is repeated, except that N-formyl-thiomorpholine is replaced by the appropriate N-formyl derivatives described in Preparation 13. This affords:
[3-(n-Propyl)-4-thiomorpholinylmethylene]-bisphosphonic acid
(3-Isopropyl-4-thiomorpholinylmethylene)-bisphosphonic acid: M.p.: 240°–241° C.
(3-Phenyl-4-thiomorpholinylmethylene)-bisphosphonic acid: M.p.: 257°–258° C. (d).
(2-Ethyl-3-methyl-4-thiomorpholinylmethylene)-bisphosphonic acid
[3-(n-Butyl)-4-thiomorpholinylmethylene]-bisphosphonic acid

EXAMPLE 7

(3-Isobutyl-4-thiomorpholinylmethylene)-bisphosphonic acid

A mixture of N-formyl-3-isobutyl-thiomorpholine (18.7 g) and phosphorous acid (16.4 g) was heated at 100° C. for 2 hours. Phosphorus trichloride (30 ml) was added dropwise with stirring, and after reflux for 3 hours water (180 ml) was added slowly. The mixture was refluxed for 1 hour and filtered. Evaporation of the filtrate gave a residue which was triturated with ethanol to yield a crystalline compound which was isolated by filtration. M.p.: 237°–238° C. (dec.).

EXAMPLE 8

The procedure of Example 7 was repeated, except that N-formyl-3-isobutyl-thiomorpholine was replaced by the appropriate N-formyl-derivative described in Preparation 13, 17 and 18. In this way the following compounds were prepared:
(3-Phenyl-4-thiomorpholinylmethylene)-bisphosphonic acid: M.p.: 257° C. (dec.).
(2-Ethyl-3-propyl-4-thiomorpholinylmethylene)-bisphosphonic acid: M.p.: 213°–215° C.
(3-Isopropyl-4-thiomorpholinylmethylene)-bisphosphonic acid: M.p.: 240°–241° C.
(2-Isopropyl-3-isobutyl-4-thiomorpholinylmethylene)-bisphosphonic acid: M.p.: 225° C.
(2,2-Dimethyl-3-isopropyl-4-thiomorpholinylmethylene)-bisphosphonic acid: M.p.: 202°–205° C.
(2,2-Dimethyl-3-phenyl-4-thiomorpholinylmethylene)-bisphosphonic acid: M.p.: 242° C.
(3-Methyl-2-phenyl-4-thiomorpholinylmethylene)-bisphosphonic acid: M.p.: 251° C. (dec.)
(3-Cyclopropyl-4-thiomorpholinylmethylene)-bisphosphonic acid: M.p.: 221° C. (dec.)
(3-Nonyl-4-thiomorpholinylmethylene)-bisphosphonic acid M.p.: 197°–200° C.
(3-Tert.butyl-4-thiomorpholinylmethylene)-bisphosphonic acid: M.p.: 217° C. (dec.).
(+)-(3-Tert.butyl-4-thiomorpholinylmethylene)-bisphosphonic acid: M.p.: 216°–217° C. (dec.). $[\alpha]_D^{20} = +33.4°$ (c=1, 1N NaOH).
(−)-(3-Tert.butyl-4-thiomorpholinylmethylene)-bisphosphonic acid: M.p.: 216°–217° C. (dec.). $[\alpha]_D^{20} = -33.8°$ (c=1, 1N NaOH).
(3-Isopentyl-4-thiomorpholinylmethylene)-bisphosphonic acid
(3-Cyclohexyl-4-thiomorpholinylmethylene)-bisphosphonic acid (+)-(3-Isobutyl-4-thiomorpholinylmethylene)-bisphosphonic acid: $[\alpha]_D^{20} = +54°$ (c=1, 1N NaOH)
(−)-(3-Isobutyl-4-thiomorpholinylmethylene)-bisphosphonic acid: $[\alpha]_D^{20} = -54.3°$ (c=1, 1N NaOH)
(2-Phenyl-3-benzyl-4-thiomorpholinylmethylene)-bisphosphonic acid
(2-pentyl-3-hexyl-4-thiomorpholinylmethylene)-bisphosphonic acid

EXAMPLE 9

Disodium (4-thiomorpholinylmethylene)-bisphosphonate sulfoxide, monohydrate

30% Aqueous hydrogen peroxide (11.1 ml) was added with stirring to a solution of (4-thiomorpholinylmethylene)-bisphosphonic acid (27.7 g) in 5M NaOH (40 ml). When the exothermic reaction had ceased the solvent was evaporated, and the residue was treated with ethanol and filtered to yield the title compound as colourless crystals. The NMR-spectrum was identical with that described in Example 5.

EXAMPLE 10

By following the procedure described in Example 9 the following sulfoxides were prepared:
Disodium ]3-(tert.butyl)-4-thiomorpholinylmethylene]-bisphosphonate sulfoxide
Disodium (3-isobutyl-4-thiomorpholinylmethylene)-bisphosphonate sulfoxide
Disodium (3-cyclopropyl-4-thiomorpholinylmethylene)-bisphosphonate sulfoxide

EXAMPLE 11

By following the procedure of Example 1, but substituting the N-formyl-derivatives of Preparation 19 and 20 for N-formyl-thiomorpholine the following compounds were prepared:
(Tetrahydro-1,4-thiazepin-4-yl-methylene)-bisphosphonic acid: M.p.: 239°–240° C.
(2-Methyl-tetrahydro-1,4-thiazepin-4-yl-methylene)-bisphosphonic acid: M.p.: 241° C.

EXAMPLE 12

Tetra-pivaloyloxymethyl (4-thiomorpholinylmethylene)-bisphosphonate

A solution of (4-thiomorpholinylmethylene)-bisphosphonic acid (2.8 g) in water (60 ml) was treated with four equivalents of aqueous tetrabutylammonium hydroxide and freeze-dried. Remaining water was removed azeotropically with toluene. The resulting salt was suspended in tetrahydrofuran (120 ml), and iodomethyl pivalate (9.4 ml) was added with stirring. After stirring for 1 hour at room temperature, the mixture was filtered, and the filtrate evaporated in vacuo. The residue was taken up in ethyl acetate and washed with aqueous sodium bicarbonate, dried and evaporated in vacuo. Chromatography on silica gel (eluent: petroleum ether—ethyl acetate 7:3) gave the pure title compound which crystallized on standing. M.p.: 86°–88° C. NMR (CDCl₃): δ=1.24 (s, 36H); 2.65 (m, 4H); 3.25 (m, 4H); 3.55 (t, J=26 Hz, 1H) and 5.70 (m, 8H) ppm.

EXAMPLE 13

Tetra-acetoxymetyl (4-thiomorpholinylmethylene)-bisphosphonate

By following the procedure described in Example 12, but substituting iodomethyl acetate for iodomethyl pivalate, the title compound was obtained as a colourless oil. NMR (CDCl₃): δ=2.14 (s, 6H); 2.16 (s, 6H); 2.65 (m, 4H); 3.26 (m, 4H); 3.53 (t, J=26 Hz, 1H) and 5.70 (m, 8H) ppm.

EXAMPLE 14

Di-pivaloyloxymetyl (4-thiomorpholinylmethylene)-bisphosphonate disodium salt

A solution of tetra-pivaloyloxymethyl (4-thiomorpholinylmethylene)-bisphosphonate (0.37 g) and sodium iodide (0.22 g) in acetone (5 ml) was refluxed for 90 minutes, cooled and filtered to yield the title compound as colourless crystals.
NMR: (D₂O): δ=1.16 (s, 18H); 2.65 (m, 4H); 3.05 (t, 1H); 3.18 (m, 4H) and 5.52 (m, 4H) ppm.

EXAMPLE 15

Di-acetoxymethyl (4-thiomorpholinylmethylene)-bisphosphonate disodium salt

This compound was prepared from tetra-acetoxymethyl (4-thiomorpholinylmethylene)-bisphosphonate by following the procedure of Example 14. NMR (D₂O): δ=2.09 (s, 6H); 2.65 (m, 4H): 3.10 (t, 1H); 3.25 (m, 4H) and 5.50 (m, 4H) ppm.

We claim:

1. A compound of the formula I

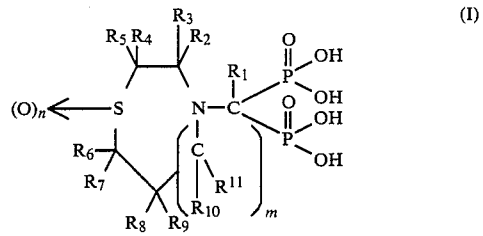

in which R₁–R₇ can be the same or different and stand for hydrogen, a straight, branched or cyclic C₁–C₁₀ hydrocarbon radical, phenyl or a phenyl -C₁–C₄-alkyl radical; R₈–R₁₁ each stand for hydrogen n is zero or one, and m is zero, one or two; and pharmaceutically acceptable salts thereof.

2. A compound according to claim 1, in which R₁–R₇, being the same or different, stand for hydrogen, C₁–C₅-alkyl or phenyl.

3. A salt according to claim 1, which is a salt of a compound of formula I with a pharmaceutically acceptable non-toxic base, such salt being selected from the group consisting of alkali metal salts, alkaline earth metal salts, or salts with ammonia or suitable non-toxic amines, such as lower alkylamines, lower alkanolamines, procaine, cycloalkylamines, benzylamines, and heterocyclic amines.

4. A compound of formula I according to claim 1, selected from the group consisting of
   (4-thiomorpholinylmethylene)-bisphosphonic acid and its salts, and
   (3-isobutyl-4-thiomorpholinylmethylene)-bisphosphonic acid in racemic form or in the form of the single enantiomers, and salts, and
   (3-tert-butyl-4-thiomorpholinylmethylene)-bisphosphonic acid in racemic form or in the form of the single enantiomers, and salts, and (2-methyl-4-thiomorpholinylmethylene)-bisphosphonic acid in racemic form or in the form of the single enantiomers, and salts.

5. A method for producing a compound of formula I of claim 1, in which a compound of formula II

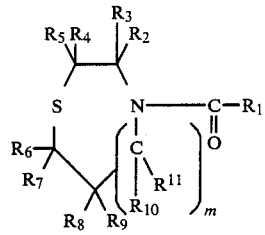

(II)

where $R_1$–$R_{11}$ and m have the meanings defined in claim 1, is transformed into an acid amide chloride which is reacted with a trialkylphosphite to form a compound of formula IV

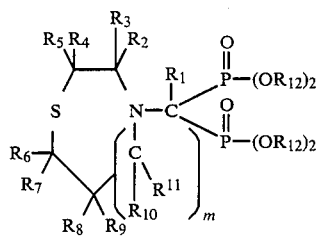

(IV)

where $R_1$–$R_{11}$ and m have the meanings defined in claim 1, and $R_{12}$ is a $C_1$–$C_4$-alkyl radical or a benzyl or a substituted benzyl radical, whereafter the compound of formula IV thus produced is hydrolyzed or hydrogenolyzed to form the desired compound of formula I (n=0), or the compound of formula IV is optionally oxidized to form a compound in which n=1, followed by a hydrolysis or hydrogenolysis as above to form the desired compound of formula I (n=1); the final compound of formula I being recovered as such or as a salt as defined in claim 1.

6. A method for producing a compound of formula I of claim 1, in which a compound of formula II, where $R_1$–$R_{11}$ and m have the meanings defined in claim 1, is heated with a mixture of phosphorous acid and phosphorus trichloride or phosphorus oxychloride followed by a hydrolysis to form the desired compound of formula I (n=0) optionally followed by an oxidation to form a compound of formula I (n=1), the final compound of formula I being recovered as such or as a salt as defined in claim 1.

7. A pharmaceutical composition, containing an effective amount of one or more of the compounds of claim 1, together with pharmaceutically acceptable, non-toxic carriers and/or auxiliary agents.

8. A method for the treatment of a patient suffering from osteoporosis, rheumatoid arthritis or other arthritic disorder, atherosclerosis, hypercalcemia due to malignancies or primary hyperparathyroidism, Pagets disease, or other condition with an abnormal calcium balance, in which a composition according to claim 7 is administered to the patient in need of treatment.

* * * * *

UNITED STATES PATENT AND TRADEMARK OFFICE
CERTIFICATE OF CORRECTION

PATENT NO. : 4,870,063

DATED : September 26, 1989

INVENTOR(S) : BINDERUP ET AL

It is certified that error appears in the above-identified patent and that said Letters Patent is hereby corrected as shown below:

In the formula in the Abstract; in the formulas in Column 1, between lines 15-25; Column 2, between lines 40-50 and 56-67; Column 3, between lines 5-15; Column 14, between lines 30-40; and Column 15, between lines 7-15 and lines 25-35, each occurrence, extend the line through the left-hand bracket to the C atom so that this portion of each formula reads:

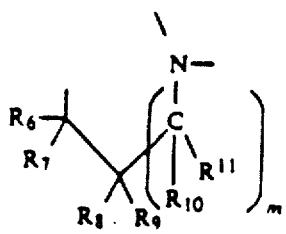

Signed and Sealed this

Twelfth Day of March, 1991

Attest:

HARRY F. MANBECK, JR.

Attesting Officer

Commissioner of Patents and Trademarks